US006958228B2

(12) United States Patent
Bathe et al.

(10) Patent No.: US 6,958,228 B2
(45) Date of Patent: Oct. 25, 2005

(54) NUCLEOTIDE SEQUENCE WHICH CODE FOR THE METH GENE

(75) Inventors: Brigitte Bathe, Salzkotten (DE); Bettina Moeckel, Duesseldorf (DE); Walter Pfefferle, Halle (DE); Klaus Huthmacher, Gelnhausen (DE); Christian Rueckert, Guetersloh (DE); Joern Kalinowski, Bielefeld (DE); Alfred Puehler, Bielefeld (DE); Michael Binder, Steinhagen (DE); Dieter Greissinger, Niddatal (DE); Georg Thierbach, Bielefeld (DE)

(73) Assignee: Degussa AG, Duesseldorf (DE)

( * ) Notice: Subject to any disclaimer, the term of this patent is extended or adjusted under 35 U.S.C. 154(b) by 449 days.

(21) Appl. No.: 09/919,891

(22) Filed: Aug. 2, 2001

(65) Prior Publication Data

US 2002/0048793 A1 Apr. 25, 2002

Related U.S. Application Data

(60) Provisional application No. 60/294,251, filed on May 31, 2001.

(30) Foreign Application Priority Data

Aug. 2, 2000 (DE) .......................... 100 38 050
Feb. 28, 2001 (DE) .......................... 101 09 687

(51) Int. Cl.[7] .......................... C12P 13/12; C12N 9/10; C12N 1/20; C12N 15/09; C07H 21/04
(52) U.S. Cl. ................... 435/113; 435/106; 435/183; 435/193; 435/252.3; 435/252.32; 435/320.1; 536/23.2
(58) Field of Search .................. 435/106, 113, 435/183, 193, 252.3, 252.32, 320.1; 536/23.2

(56) References Cited

U.S. PATENT DOCUMENTS

2003/0049804 A1   3/2003   Pompejus et al.

FOREIGN PATENT DOCUMENTS

| DE | 196 44 567 | 4/1998 |
| EP | 0 387 527 | 9/1990 |
| EP | 1108790 A2 | 6/2001 |
| EP | 1 108 790 | 6/2001 |
| WO | WO 93/17112 | 9/1993 |
| WO | WO 01/00802 | 1/2001 |
| WO | WO 01/00843 | 1/2001 |
| WO | WO 01/00845 | 1/2001 |
| WO | WO 01/00847 | 1/2001 |

OTHER PUBLICATIONS

Attwood et al. Which craft is best in bioformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
Eiglmeier et al. GenBank Accession AL035310. Aug. 27, 1999.*
Strausberg. Accession AW576625, Mar. 15, 2000.*
Eiglmeier et al. Accession AL035310. Aug. 27, 1999 (Alignment No. 1).*
Eiglmeier et al. Accession AL035310. Aug. 27, 1999 (Alignment No. 2).*
S. T. Cole, et al., Swiss–Prot, pp. 1–2, XP 002175756, "5–Methyltetrahydrofolate–Homoysteine Methyltransferase of *Mycobacterium Tuberculosis* (EC 2.1.1.13)", Jul. 15, 1998.
T. Hishino, Database EMBL Online, pp. 1–2, XP 002185491, Accession No. AB029371, "Analysis of Methionine Biosynthetic Pathway in Thermus Thermophilus", Jan. 7, 2000.
Derwent Abstracts, KR 9 208 381, Sep. 26, 1992.
Derwent Abstracts, WO 01/00843, Jan. 4, 2001.
Reinhard Kraemer, Journal of Biotechnology, vol. 45, No. 1, pp. 1–21, "Genetic and Physiological Approaches for the Production of Amino Acids", 1996.
Lain G. Old, et al., Journal of Bacteriology, vol. 175, No. 11, pp. 3689–3691, "Physical Mapping of the Scattered Methionine Genes on the *Escherichia Coli* Chromosome", Jun. 1993.

* cited by examiner

*Primary Examiner*—Manjunath N Rao
*Assistant Examiner*—Christian L. Fronda
(74) *Attorney, Agent, or Firm*—Oblon, Spivak, McClelland, Maier & Neustadt, P.C.

(57) ABSTRACT

An isolated polynucleotide comprising a polynucleotide sequence selected from the group consisting of
a) polynucleotide which is at least 70% identical to a polynucleotide that codes for a polypeptide which comprises the amino acid sequence of SEQ ID No. 2,
b) polynucleotide which codes for a polypeptide that comprises an amino acid sequence which is at least 70% identical to the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c),
and processes for the fermentative preparation of L–amino acids using coryneform bacteria in which at least the metH gene is present in enhanced form, and use of the polynucleotide sequences as hybridization probes.

44 Claims, 1 Drawing Sheet

Figure 1: Plasmid pCREmetH
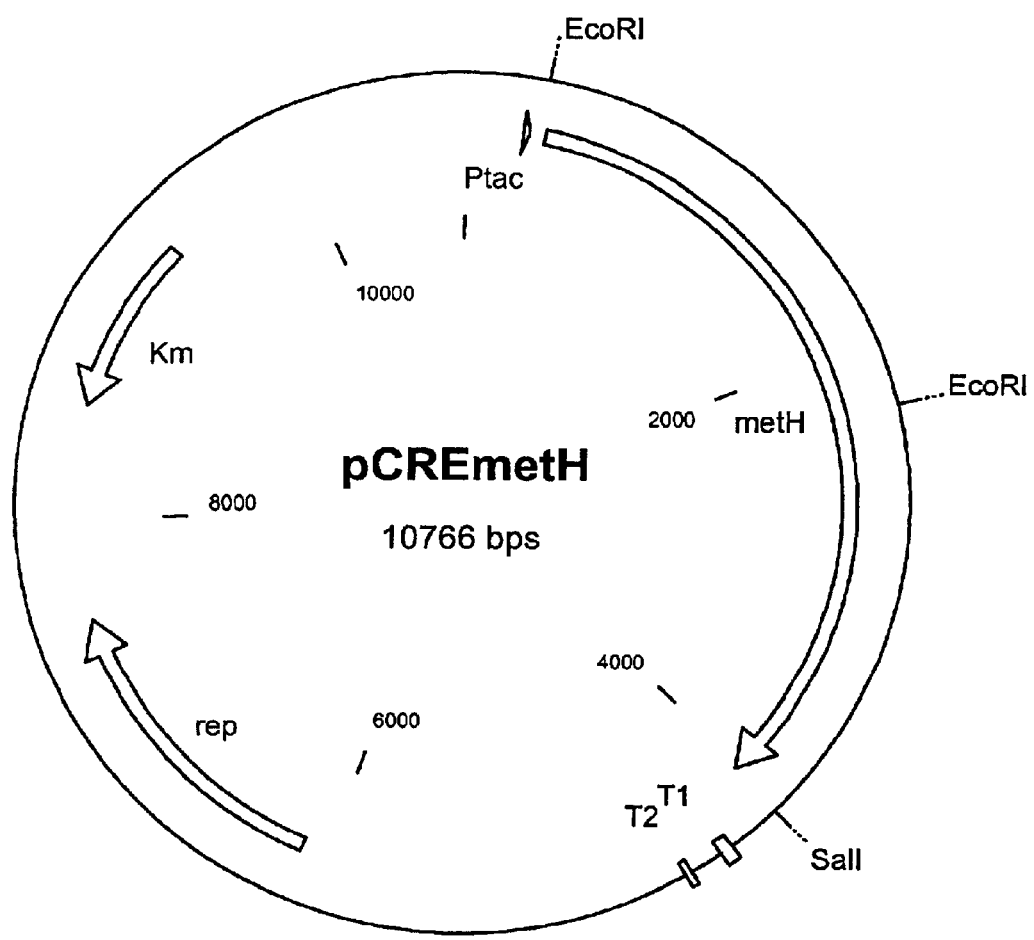

NUCLEOTIDE SEQUENCE WHICH CODE FOR THE METH GENE

BACKGROUND OF THE INVENTION

1. Field of the Invention

The invention provides nucleotide sequences from coryneform bacteria which code for the metH gene and a process for the fermentative preparation of amino acids, in particular L-methionine, using bacteria in which the metH gene is enhanced.

2. Description of the Related Art

L-Amino acids, in particular L-methionine, are used in human medicine and in the pharmaceuticals industry, in the foodstuffs industry and very particularly in animal nutrition.

It is known that amino acids are prepared by fermentation from strains of coryneform bacteria, in particular *Corynebacterium glutamicum*. Because of their great importance, work is constantly being undertaken to improve the preparation process. Improvements to the process can relate to fermentation measures, such as, stirring and supply of oxygen, or to the composition of the nutrient media, such as, the sugar concentration during the fermentation, or to the working up of the product by, for example, ion exchange chromatography, or to the intrinsic output properties of the microorganism itself.

Methods of mutagenesis, selection and mutant selection are used to improve the output properties of these microorganisms. Strains which are resistant to antimetabolites, such as e.g. the methionine analogue α-methyl-methionine, ethionine, norleucine, N-acetylnorleucine, S-trifluoromethylhomocysteine, 2-amino-5-heprenoitic acid, seleno-methionine, methionine-sulfoximine, methoxine, 1-aminocyclopentane-carboxylic acid, or are auxotrophic for metabolites of regulatory importance and produce amino acids, such as e.g. L-methionine, are obtained in this manner.

Recombinant DNA techniques have also been employed for some years for improving *Corynebacterium* strains which produce L-amino acids, by amplifying individual amino acid biosynthesis genes and investigating their effect on the amino acid production.

SUMMARY OF THE INVENTION

One object of the present invention is to provide new measures for improved fermentative preparation of amino acids, in particular L-methionine.

When L-methionine or methionine are mentioned in the following, the salts, such as methionine hydrochloride or methionine sulfate are also meant.

The invention provides an isolated polynucleotide from *coryneform bacteria*, comprising a polynucleotide sequence which codes for the metH gene, chosen from the group consisting of a) polynucleotide which is at least 70% identical to a polynucleotide that codes for a polypeptide which comprises the amino acid sequence of SEQ ID No. 2,
b) polynucleotide which codes for a polypeptide that comprises an amino acid sequence which is at least 70% identical to the amino acid sequence of SEQ ID No. 2,
c) polynucleotide which is complementary to the polynucleotides of a) or b), and
d) polynucleotide comprising at least 15 successive nucleotides of the polynucleotide sequence of a), b) or c), and the corresponding polypeptides having the enzymatic activity of homocysteine methyltransferase II.

The invention also provides the above-mentioned polynucleotides, as DNA which is capable of replication, comprising:

(i) the nucleotide sequence shown in SEQ ID No. 1, or
(ii) at least one sequence which corresponds to sequence (i) within the range of the degeneration of the genetic code, or
(iii) at least one sequence which hybridizes with the sequence complementary to sequence (i) or (ii), and optionally
(iv) sense mutations of neutral function in (i).

The invention also provides a polynucleotide comprising the nucleotide sequence as shown in SEQ ID No. 1;
a polynucleotide that codes for a polypeptide which comprises the amino acid sequence as shown in SEQ ID No. 2,
a vector containing the polynucleotide according to the invention, in particular a shuttle vector or plasmid vector, and
and coryneform bacteria serving as the host cell, which contain the vector or in which the metH gene is enhanced.

The invention also provides polynucleotides which are obtained by screening a corresponding gene library, which comprises the complete gene having the polynucleotide sequence corresponding to SEQ ID No. 1, by means of hybridization with a probe which comprises the sequence of the polynucleotide mentioned, according to SEQ ID No. 1 or a fragment thereof, and isolation of the DNA sequence mentioned.

BRIEF DESCRIPTION OF THE FIGS.

FIG. 1 shows plasmid pCREmetH.

DETAILED DESCRIPTION OF THE PREFERRED EMBODIMENTS

Polynucleotides according to the invention are suitable as hybridization probes for RNA, cDNA and DNA, in order to isolate, in the full length, nucleic acids or polynucleotides or genes which code for homocysteine methyltransferase II or to isolate those nucleic acids or polynucleotides or genes which have a high similarity of sequence or homology with that of the homocysteine methyltransferase II gene.

Polynucleotides according to the invention are furthermore suitable as primers with the aid of which DNA of genes that code for homocysteine methyltransferase II can be prepared by the polymerase chain reaction (PCR).

Such oligonucleotides that serve as probes or primers comprise at least 30, preferably at least 20, very particularly at least 15 successive nucleotides. Oligonucleotides which have a length of at least 40 or 50 nucleotides are also suitable. oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

"Polypeptides" are understood as meaning peptides or proteins which comprise two or more amino acids bonded via peptide bonds.

The polypeptides according to the invention include a polypeptide according to SEQ ID No. 2, in particular those with the biological activity of homocysteine methyltransferase II, and also those which are at least 70%, preferably at least 80% and in particular which are at least 90% to 95% identical to the polypeptide according to SEQ ID No. 2 and have the activity mentioned.

The invention moreover provides a process for the fermentative preparation of amino acids, in particular L-methionine, using coryneform bacteria which in particular already produce amino acids, and in which the nucleotide sequences which code for the metH gene are enhanced, in particular over-expressed.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on the starting microorganism.

The microorganisms which the present invention provides can prepare L-amino acids, in particular L-methionine, from glucose, sucrose, lactose, fructose, maltose, molasses, starch, cellulose or from glycerol and ethanol. They can be representatives of *coryneform bacteria*, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains Corynebacterium glutamicum ATCC13032
Corynebacterium acetoglutamicum ATCC15806
Corynebacterium acetoacidophilum ATCC13870
Corynebacterium thermoaminogenes FERM BP-1539
Corynebacterium melassecola ATCC17965
Brevibacterium flavum ATCC14067
Brevibacterium lactofermentum ATCC13869 and
Brevibacterium divaricatum ATCC14020 or L-amino acid-producing mutants or strains prepared therefrom, such as, for example, the L-methionine-producing strain Corynebacterium glutamicum ATCC21608.

The new metH gene from *C. glutamicum* which codes for the enzyme homocysteine methyltransferase II (EC 2.1.1.13) has been isolated.

To isolate the metH gene or also other genes of *C. glutamincum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie (Verlag Chemie, Weinheim, Germany, 1990), or the handbook by Sambrook et al.: Molecular Cloning, A Laboratory Manual (Cold Spring Harbor Laboratory Press, 1989) may be mentioned as examples. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamincum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326) (1992)) in turn describe a gene library of *C. glutamincum* ATCC13032 using the cosmid pHC79 (Hohn and Collins, Gene 11, 291–298 (1980)). To prepare a gene library of *C. glutamincum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DH5 αmcr, which has been described by Grant et al. (Proceedings of the National Academy of Sciences USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamincum* which codes for the metH gene and which, as SEQ ID No. 1, is a constituent of the present invention has been found. The amino acid sequence of the corresponding protein has furthermore been derived from the present DNA sequence by the methods described above. The resulting amino acid sequence of the metH gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. they are of neutral function.

It is furthermore known that changes at the N and/or C terminus of a protein must not substantially impair and may even stabilize the function thereof. Information in this context can be found in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). Instructions for amplification of DNA sequences with the aid of the polymerase chain reaction (PCR) can be found in the handbook by Gait:

Oligonucleotide Synthesis: A Practical Approach (IRL Press, Oxford, UK, 1984) and in Newton and Graham: PCR (Spektrum Akademischer Verlag, Heidelberg, Germany, 1994).

It has been found that coryneform bacteria produce amino acids, in particular L-methionine, in an improved manner after over-expression of the metH gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative L-methionine production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European Patent Specification 0 472 869, in U.S. Pat. No. 4,601,893, in Schwarzer and Pühler (Bio/Technology 9, 84–87 (1991)), in Reinscheid et al. (Applied and Environmental 5 Microbiology 60, 126–132 (1994)), in LaBarre et al. (Journal of Bacteriology 175, 1001–1007 (1993)), in Patent Application WO 96/15246, in Malumbres et al. (Gene 134, 15–24 (1993)), in Japanese Laid-Open Specification JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the metH gene according to the invention was over-expressed with the aid of episomal plasmids. Suitable plasmids are those which are replicated in coryneform bacteria. Numerous known plasmid vectors, such as e.g. pZl (Menke1 et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically E. coli), but not in C. glutamicum. Possible vectors are, for example, pSUP301 (Simon et al., Bio/Technology 1, 784–791 (1983)), pK18mob or pK19mob (Schäfer et al., Gene 145, 69–73 (1994)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al.,1986, Gene 41: 337–342). The plasmid vector which contains the gene to be amplified is then transferred into the desired strain of C. glutamincum by conjugation or transformation. The method of conjugation is described, for example, by Schäfer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of amino acids, in particular L-methionine, to enhance one or more enzymes of the particular biosynthesis pathway, of glycolysis, of anaplerosis, of the citric acid cycle or of amino acid export, in addition to the metH gene.

Thus for the preparation of amino acids, in particular L-methionine, one or more genes chosen from the group consisting of the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the pyc gene which codes for pyruvate carboxylase (Eikmanns (1992), Journal of Bacteriology 174:6076–6086), the lysC gene which codes for a feed-back resistant aspartate kinase (ACCESSION NUMBER P26512; EP-B-0387527; EP-A-0699759), the metA gene which codes for homoserine O-acetyltransferase (ACCESSION Number AF052652), the metB gene which codes for cystathionine gamma-synthase (ACCESSION Number AF126953), the aecD gene which codes for cystathionine gamma-lyase (ACCESSION Number M89931)

the glyA gene which codes for serine hydroxymethyl-transferase (JP-A-08107788), the metY gene which codes for O-acetylhomoserine-sulfhydrylase (DSM 13556)

can be enhanced, in particular over-expressed.

It may furthermore be advantageous for the production of amino acids, in particular L-methionine, in addition to the enhancement of the metH gene, for one or more genes chosen from the group consisting of the thrB gene which codes for homoserine kinase (ACCESSION Number P08210), the ilvA gene which codes for threonine dehydratase (ACCESSION Number Q04513), the thrC gene which codes for threonine synthase (ACCESSION Number P23669), the ddh gene which codes for meso-diaminopimelate D-dehydrogenase (ACCESSION Number Y00151), the pck gene which codes for phosphoenol pyruvate carboxykinase (DE 199 50 409.1; DSM 13047), the pgi gene which codes for glucose 6-phosphate isomerase (U.S. Ser. No. 09/396,478; DSM 12969), the poxB gene which codes for pyruvate oxidase (DE: 1995 1975.7; DSM 13114)

to be attenuated, in particular for the expression thereof to be reduced.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 50%, 0 to 25%, 0 to 10% or 0 to 5% of the activity or concentration of the wild-type protein.

In addition to over-expression of the metH gene it may furthermore be advantageous for the production of amino acids, in particular L-methionine, to eliminate undesirable side reactions, (Nakayama: "Breeding of Amino Acid Producing Micro-organisms", in: Overproduction of Microbial Products, Krumphanzl, Sikyta, Vanek (eds.), Academic Press, London, UK, 1982).

The microorganisms prepared according to the invention can be cultured continuously or discontinuously in the batch process (batch culture) or in the fed batch (feed process) or repeated fed batch process (repetitive feed process) for the purpose of production of amino acids, in particular L-methionine. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Organic and inorganic sulfur-containing compounds, such as, for example, sulfides, sulfites, sulfates and thiosulfates, can be used as a source of sulfur, in particular for the preparation of methionine.

Phosphoric acid, potassium dihydrogen phosphate or dipotassium hydrogen phosphate or the corresponding sodium-containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

The fermentation broths obtained in this way, in particular containing L-methionine, usually have a dry weight of 7.5 to 25 wt. % and contain L-methionine. It is furthermore also advantageous if the fermentation is conducted in a sugar-limited procedure at least at the end, but in particular over at least 30% of the duration of the fermentation. That is to say, the concentration of utilizable sugar in the fermentation medium is reduced to $\geq 0$ to 3 g/l during this period.

The fermentation broth prepared in this manner, in particular containing L-methionine, is then further processed. Depending on requirements all or some of the biomass can be removed from the fermentation broth by separation methods, such as centrifugation, filtration, decanting or a combination thereof, or it can be left completely in. This broth is then thickened or concentrated by known methods, such as with the aid of a rotary evaporator, thin film evaporator, falling film evaporator, by reverse osmosis, or by nanofiltration. This concentrated fermentation broth can then be worked up by methods of freeze drying, spray drying, spray granulation or by other processes to give a preferably free-flowing, finely divided powder.

This free-flowing, finely divided powder can then in turn by converted by suitable compacting or granulating processes into a coarse-grained, readily free-flowing, storable and largely dust-free product. In the granulation or compacting it is advantageous to employ conventional organic or inorganic auxiliary substances or carriers, such as starch, gelatin, cellulose derivatives or similar substances, such as are conventionally used as binders, gelling agents or thickeners in foodstuffs or feedstuffs processing, or further substances, such as, for example, silicas, silicates or stearates.

"Free-flowing" is understood as meaning powders which flow unimpeded out of the vessel with the opening of 5 mm (millimeters) of a series of glass outflow vessels with outflow openings of various sizes (Klein, Seifen, Öle, Fette, Wachse 94, 12 (1968)).

As described here, "finely divided" means a powder with a predominant content (>50%) having a particle size of 20 to 200 μm diameter. "Coarse-grained" means products with a predominant content (>50%) having a particle size of 200 to 2000 μm diameter. In this context, "dust-free" means that the product contains only small contents (<5%) having particle sizes of less than 20 μm diameter. The particle size determination can be carried out with methods of laser diffraction spectrometry. The corresponding methods are described in the textbook on "Teilchengrößenmessung in der Laborpraxis" by R. H. Müller and R. Schuhmann, Wissenschaftliche Verlagsgesellschaft Stuttgart (1996) or in the textbook "Introduction to Particle Technology" by M. Rhodes, Verlag Wiley & Sons (1998).

"Storable" in the context of this invention means a product which can be stored for up to 120 days, preferably up to 52 weeks, particularly preferably 60 months, without a substantial loss (<5%) of methionine occurring.

Alternatively, however, the product can be absorbed on to an organic or inorganic carrier substance which is known and conventional in feedstuffs processing, for example, silicas, silicates, grits, brans, meals, starches, sugars or others, and/or mixed and stabilized with conventional thickeners or binders. Use examples and processes in this context are described in the literature (Die Mühle±Mischfuttertechnik 132 (1995) 49, page 817).

Finally, the product can be brought into a state in which it is stable to digestion by animal stomachs, in particular the stomach of ruminants, by coating processes ("coating") using film-forming agents, such as, for example, metal carbonates, silicas, silicates, alginates, stearates, starches, gums and cellulose ethers, as described in DE-C-4100920.

If the biomass is separated off during the process, further inorganic solids, for example added during the fermentation, are in general removed. In addition, the animal feedstuffs additive according to the invention comprises at least the predominant proportion of the further substances, in particular organic substances, which are formed or added and are present in solution in the fermentation broth, where these have not been separated off by suitable processes.

In one aspect of the invention, the biomass can be separated off to the extent of up to 70%, preferably up to 80%, preferably up to 90%, preferably up to 95%, and particularly preferably up to 100%. In another aspect of the invention, up to 20% of the biomass, preferably up to 15%, preferably up to 10%, preferably up to 5%, particularly preferably no biomass is separated off.

These organic substances include organic by-products which are optionally produced, in addition to the L-methionine, and optionally discharged by the microorganisms employed in the fermentation. These include L-amino acids chosen from the group consisting of L-lysine, L-valine, L-threonine, L-alanine or L-tryptophan. They include vitamins chosen from the group consisting of vitamin B1 (thiamine), vitamin B2 (riboflavin), vitamin B5 (pantothenic acid), vitamin B6 (pyridoxine), vitamin B12 (cyanocobalamin), nicotinic acid/nicotinamide and vitamin E (tocopherol). They also include organic acids which carry one to three carboxyl groups, such as acetic acid, lactic acid, citric acid, malic acid or fumaric acid. Finally, they also include sugars, for example, trehalose. These compounds are optionally desired if they improve the nutritional value of the product.

These organic substances, including L-methionine and/or D-methionine and/or the racemic mixture D,L-methionine, can also be added, depending on requirements, as a concentrate or pure substance in solid or liquid form during a suitable process step. These organic substances mentioned can be added individually or as mixtures to the resulting or concentrated fermentation broth, or also during the drying or granulation process. It is likewise possible to add an organic substance or a mixture of several organic substances to the fermentation broth and a further organic substance or a further mixture of several organic substances during a later process step, for example granulation.

The product described above is suitable as a feedstuffs additive, i.e. feed additive, for animal nutrition.

The L-methionine content of the animal feedstuffs additive is conventionally 1 wt. % to 80 wt. %, preferably 2 wt. % to 80 wt. %, particularly preferably 4 wt. % to 80 wt. %, and very particularly preferably 8 wt. % to 80 wt. %, based on the dry weight of the animal feedstuffs additive. Contents of 1 wt. % to 60 wt. %, 2 wt. % to 60 wt. %, 4 wt. % to 60 wt. %, 6 wt. % to 60 wt. %, 1 wt. % to 40 wt. %, 2 wt. % to 40 wt. % or 4 wt. % to 40 wt. % are likewise possible. The water content of the feedstuffs additive is conventionally up to 5 wt. %, preferably up to 4 wt. %, and particularly preferably less than 2 wt. %.

The invention also provides a process for the preparation of an L-methionine-containing animal feedstuffs additive from fermentation broths, which comprises the steps a) culture and fermentation of an L-methionine-producing microorganism in a fermentation medium;

b) removal of water from the L-methionine-containing fermentation broth (concentration);

c) removal of an amount of 0 to 100 wt. % of the biomass formed during the fermentation; and d) drying of the fermentation broth obtained according to a) and/or b) to obtain the animal feedstuffs additive in the desired powder or granule form.

If desired, one or more of the following steps can furthermore be carried out in the process according to the invention:

e) addition of one or more organic substances, including L-methionine and/or D-methionine and/or the racemic mixture D,L-methionine, to the products obtained according to a), b) and/or c);

f) addition of auxiliary substances chosen from the group consisting of silicas, silicates, stearates, grits and bran to the substances obtained according to a) to d) for stabilization and to increase the storability; or g) conversion of the substances obtained according to a) to e) into a form stable to the animal stomach, in particular rumen, by coating with film-forming agents.

The analysis of L-methionine can be carried out by ion exchange chromatography with subsequent ninhydrin derivation, as described by Spackman et al. (Analytical Chemistry, 30, (1958), 1190).

The process according to the invention is used for the fermentative preparation of amino acids, in particular L-methionine.

The following microorganism was deposited as a pure culture on 14th June 2001 at the Deutsche Sammlung für Mikroorganismen und Zellkulturen (DSMZ=German Collection of Microorganisms and Cell Cultures, Braunschweig, Germany) in accordance with the Budapest Treaty:

*Escherichia coli* DH5βxmcr/pCREmetH as DSM 14354.

The present invention is explained in more detail in the following with the aid of embodiment examples.

EXAMPLE 1

Preparation of a Genomic Cosmid Gene Library from *Corynebacterium glutamicum*ATCC 13032

Chromosomal DNA from *Corynebacterium glutamicum*ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250).

The DNA of the cosmid vector SuperCos1 (Wahl et al. (1987) Proceedings of the National Academy of Sciences USA 84:2160–2164), obtained from Stratagene (La Jolla, USA, Product Description SuperCosI Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase. The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the E. coli strain NM554 (Raleigh et al. 1988, Nucleic Acid Research 16:1563–1575) the cells were taken up in 10 mM $MgSO_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 mg/l ampicillin. After incubation overnight at 37° C., recombinant individual clones were selected.

EXAMPLE 2

Isolation and Sequencing of the metH Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, The Netherlands, Product Description Zero Background Cloning Kit, Product No. K2500-01) was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343-7) into the E. coli strain DH5 αmcr (Grant, 1990, Proceedings of the National Academy of Sciences U.S.A., 87:4645–4649) and plated out on LB agar (Lennox, 1955, Virology, 1:190) with 50 mg/l zeocin.

The plasmid preparation of the recombinant clones was carried out with Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/ Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pzerol derivatives were assembled to a continuous contig. The computer-assisted coding region analysis was prepared with the XNIP program (Staden, 1986, Nucleic Acids Research, 14:217–231).

The resulting nucleotide sequence is shown in SEQ ID No. 1. Analysis of the nucleotide sequence showed an open reading frame of 3662 base pairs, which was called the metH gene. The metH gene codes for a protein of 1221 amino acids.

EXAMPLE 3

Preparation of the Strain C. glutamincum ATCC13032/ pCREmetH 3.1 μmplification of the metH Gene From the strain ATCC13032, chromosomal DNA was isolated by the method of Eikmanns et al. (Microbiology 140: 1817–1828 (1994)). Starting from the nucleotide sequences of the methionine biosynthesis genes metH (SEQ ID No. 1) of C. glutamicum ATCC13032, the following oligonucleotides were chosen for the polymerase chain reaction (PCR) (see SEQ ID No. 3 and SEQ ID No. 4):

metH-EVP5:
5'-GATCTA<u>AGATCT</u>AAAGGAGGACAACCAT-
GTCTACTTCAGTTACTTCACCAGC-3'
metH-EVP3:
5'-GATCTA<u>GTCGAC</u>CCCTCTCAAAGGTGTTAGAC-3'

The primers shown were synthesized by MWG-Biotech AG (Ebersberg, Germany) and the PCR reaction was carried out by the standard PCR method of Innis et al. (PCR Protocols. A Guide to Methods and Applications, 1990, Academic Press) with Pwo-Polymerase from Roche Diagnostics GmbH (Mannheim, Germany). With the aid of the polymerase chain reaction, the primers allow amplification of a DNA fragment 3718 bp in size, which carries the metH gene.

Furthermore, the primer metH-EVP5 contains the sequence for the cleavage site of the restriction endonuclease BglII and the primer metH-EVP3 the cleavage site of the restriction endonuclease SalI, which are marked by underlining in the nucleotide sequence shown above.

The metH fragment 3718 bp in size was cleaved with the restriction endonucleases BglII and SalI. The batch was separated by gel electrophoresis and the metH fragment (approx. 3700 bp) was then isolated from the agarose gel with the QiaExII Gel Extraction Kit (Product No. 20021, Qiagen, Hilden, Germany).

3.2 Cloning of metH in the vector pZ8-1

The E. coli—C. glutamincum shuttle expression vector pZ8-1 (EP 0 375 889) was used as the base vector for the expression.

DNA of the plasmid pZ8-1 was cleaved completely with the restriction enzymes BamHI and SalI and then dephosphorylated with shrimp alkaline phosphatase (Roche Diagnostics GmbH, Mannheim, Germany, Product Description SAP, Product No. 1758250).

The metH fragment approx. 3700 bp in size isolated from the agarose gel in example 3.1 and cleaved with the restriction endonucleases BglII and SalI was mixed with the vector pZ8-1 prepared in this way and the batch was treated with T4 DNA ligase (Amersham Pharmacia, Freiburg, Germany, Product Description T4-DNA-Ligase, Code no.27-0870-04).

The ligation batch was transformed in the *E. coli* strain DH5mcr (Hanahan, In: DNA cloning. A Practical Approach. Vol. I. IRL-Press, Oxford, Washington D.C., USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and checked by restriction cleavage. The resulting plasmid was called pCREmetH. The strain *E. coli* DH5αmcr/pCREmetH was deposited as a pure culture on Jun. 14, 2001 at the Deutsche Sammlung für Mikroorganismen und Zellkulturen (DSMZ=German Collection of Microorganisms and Cell Cultures, Braunschweig, Germany) in accordance with the Budapest Treaty as DSM 14354.

3.3 Preparation of the strain *C. glutamincum* ATCC13032/pCREmetH

The vector pCREmetH obtained in example 3.2 was electroporated in the strain *C. glutamincum* ATCC13032 using the electroporation method described by Liebl et al. (FEMS Microbiology Letters, 53:299–303 (1989)). Selection of the plasmid-carrying cells took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology 144, 915–927) and checked by restriction cleavage. The resulting strain was called ATCC13032pCREmetH.

EXAMPLE 4

Preparation of methionine with the strain *C. glutamincum* ATCC13032/pCREmetH

The *C. glutamincum* strain ATCC13032/pCREmetH obtained in example 3 was cultured in a nutrient medium suitable for the production of methionine and the methionine content in the culture supernatant was determined.

For this, the strain was first incubated on an agar plate with the corresponding antibiotic (brain-heart agar with kanamycin (25 mg/l)) for 24 hours at 33° C. Starting from this agar plate culture, a preculture was seeded (10 ml medium in a 100 ml conical flask). The medium MM was used as the medium for the preculture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| Salts: | |
| $(NH_4)_2SO_4$ | 25 g/l |
| $KH_2PO_4$ | 0.1 g/l |
| $MgSO_4*7 H_2O$ | 1.0 g/l |
| $CaCl_2*2 H_2O$ | 10 mg/l |
| $FeSO_4*7 H_2O$ | 10 mg/l |
| $MnSO_4*H_2O$ | 5.0 mg/l |
| Biotin (sterile-filtered) | 0.01 mg/l |

| -continued | |
|---|---|
| Medium MM | |
| Vitamin B12 (sterile-filtered) | 0.02 mg/l |
| Thiamine*HCl (sterile-filtered) | 0.2 mg/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1. Medium MM was also used for the main culture.

Culturing is carried out in a 10 ml volume in a 100 ml conical flask with baffles. Kanamycin (25 mg/l) was added. Culturing was carried out at 33° C. and 80% atmospheric humidity. After 72 hours, the OD was determined at a measurement wavelength of 660 nm with a Biomek 1000 (Beckmann Instruments GmbH, Munich). The amount of methionine formed was determined with an amino acid analyzer from Eppendorf-BioTronik (Hamburg, Germany) by ion exchange chromatography and post-column derivation with ninhydrin detection.

The result of the experiment is shown in table 1.

TABLE 1

| Strain | OD (660 nm) | Methionine mg/l |
|---|---|---|
| ATCC13032 | 12.3 | 1.4 |
| ATCC13032/pCREmetH | 14.3 | 5.3 |

BRIEF DESCRIPTION OF THE FRIGURE

FIG. 1: Plasmid pCREmetH

The abbreviations used in the figures have the following meaning:

Km: Resistance gene for kanamycin
metH: metH gene of *C. glutamincum*
Ptac: tac promoter
T1 T2: Terminator T1T2 of the rrnB gene of *E. coli*
rep: Plasmid-coded replication origin for *C. glutamicum* (of pHM1519)
EcoRI: Cleavage site of the restriction enzyme EcoRI
SalI: Cleavage site of the restriction enzyme SalI This disclosure is based on priority documents DE 100 38 050.6, DE 101 09 687.9 and U.S. Pat. No. 60/294,251, each incorporated by reference.

Obviously, numerous modifications of the invention are possible in view of the above teachings. Therefore, within the scope of the appended claims, the invention may be practiced otherwise than as specifically described herein.

What is claimed is:

1. An isolated polynucleotide which encodes a protein comprising the amino acid sequence of SEQ ID NO: 2.

2. A vector comprising the isolated polynucleotide of claim 1.

3. A host cell transformed with the isolated polynucleotide of claim 1.

4. The host cell of claim 3, which is a coryneform bacterium.

5. The host cell of claim 3, selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum,* and *Brevibacterium divaricatum*.

6. An isolated polynucleotide, which comprises SEQ ID NO: 1 or a fragment of SEQ ID NO: 1 which encodes a polypeptide having homocysteine methyltransferase activity.

7. A vector comprising the isolated polynucleotide of claim 6.

8. A host cell transformed with the isolated polynucleotide of claim 6.

9. The host cell of claim 8, which is a coryneform bacterium.

10. The host cell of claim 8, selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum, and Brevibacterium divaricatum.

11. An isolated polynucleotide,
   which hybridizes under stringent conditions to a polynucleotide comprising SEQ ID NO: 1 or the complement thereof; wherein said stringent conditions comprise washing in 0.5 X SSC at a temperature of 68° C., and
   which encodes a protein which has homocysteine methyltransferase activity.

12. A vector comprising the isolated polynucleotide of claim 11.

13. A host cell transformed with the isolated polynucleotide of claim 11.

14. The host cell of claim 13, which is a coryneform bacterium.

15. The host cell of claim 13, selected from the group consisting of Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum, and Brevibacterium divaricatum.

16. An isolated polynucleotide
   which is at least 95% identical to a polynucleotide comprising SEQ ID NO: 1 and
   which encodes a protein having homocysteine methyltransferase activity, or
   a fragment of said polynucleotide which encodes a polypeptide having homocysteine methyltransferase activity.

17. The isolated polynucleotide of claim 16, which is at least 99% identical to the polynucleotide comprising SEQ ID NO: 1.

18. A vector comprising the isolated polynucleotide of claim 16 or 17.

19. A host cell transformed with the isolated polynucleotide of claim 16 or 17.

20. The host cell of claim 19, which is a coryneform bacterium.

21. The host cell of claim 19, selected from the group consisting of Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum, and Brevibacterium divaricatum.

22. A process for producing an L-amino acid which is L-methionine, comprising:
   culturing the host cell of claim 3 in a medium suitable for producing L-methionine; and
   collecting the L-methionine produced, wherein the isolated polynucleotide encoding SEQ ID NO: 2 is overexpressed in said host cell.

23. The process of claim 22, wherein said host cell is a coryneform bacterium.

24. The process of claim 22, wherein the host cell further comprises at least one overexpressed gene selected from the group consisting of the lysC gene which codes for a feed back resistant aspartate kinase, the gap gene which codes for glycerolaldehyde 3-phosphate dehydrogenase, the pgk gene which codes for 3-phosphoglycerate kinase, the pyc gene which codes for pyruvate carboxylase, the tpi gene which codes for triose phosphate isomerase, the metA gene which codes for homoserine O-acetyltransferase, the metB gene which codes for cystathionine gamma-synthase, the aecD gene which codes for cystathionine gamma-lyase, the glyA gene which codes for serine hydroxymethyltransferase, and the metY gene which codes for O-acetylhomoserine-sulfhydrylase.

25. The process of claim 22, wherein the host cell comprises expression of at least one gene whose expression is reduced relative to expression in a wildtype host cell, wherein the at least one gene is selected from the group consisting of the thrB gene which codes for homoserine kinase, the ilvA gene which codes for threonine dehydratase, the thrC gene which codes for threonine synthase, the ddh gene which codes for meso-diaminopimelate D-dehydrogenase, the pck gene which codes for phosphoenol pyruvate carboxykinase, the pgi gene which codes for glucose 6-phosphate isomerase, and the poxB gene which codes for pyruvate oxidase.

26. The process of claim 22, further comprising:
   removing an amount of 0 to 100 wt. % of the biomass formed during the culturing from the medium; and optionally
   concentrating the resulting medium containing the L-methionine, and optionally, drying to concentrated medium.

27. A process for producing an L-amino acid which is L-methionine, comprising
   culturing the host cell of claim 8 in a medium suitable for producing L-methionine; and
   collecting the L-methionine produced, wherein the isolated polynucleotide is overexpressed in said host cell.

28. The process of claim 27, wherein said host cell is a coryneform bacterium.

29. The process of claim 27, wherein the host cell further comprises at least one overexpressed gene selected from the group consisting of the lysC gene which codes for a feed back resistant aspartate kinase, the gap gene which codes for glycerolaldehyde 3-phosphate dehydrogenase, the pgk gene which codes for 3-phosphoglycerate kinase, the pyc gene which codes for pyruvate carboxylase, the tpi gene which codes for triose phosphate isomerase, the metA gene which codes for homoserine O-acetyltransferase, the metB gene which codes for cystathionine gamma-synthase, the aecD gene which codes for cystathionine gamma-lyase, the glyA gene which codes for serine hydroxymethyltransferase, and the metY gene which codes for O-acetylhomoserine-sulfhydrylase.

30. The process of claim 27, wherein the host cell comprises at least one gene whose expression is reduced relative to expression in a wildtype host cell, wherein the at least one gene is selected from the group consisting of the thrB gene which codes for homoserine kinase, the ilvA gene which codes for threonine dehydratase, the thrC gene which codes for threonine synthase, the ddh gene which codes for meso-diaminopimelate D-dehydrogenase, the pck gene which codes for phosphoenol pyruvate carboxykinase, the pgi gene which codes for glucose 6-phosphate isomerase, and the poxB gene which codes for pyruvate oxidase.

31. The process of claim 27, further comprising:
   removing an amount of 0 to 100 wt. % of the biomass formed during the culturing from the medium;
   concentrating the resulting medium containing the L-methionine; and optionally drying the concentrated medium.

32. A process for producing an L-amino acid which is L-methionine comprising
   culturing the host cell of claim 13 in a medium suitable for producing L-methionine; and collecting the L-methionine produced, wherein the isolated polynucleotide is overexpressed in said host cell.

33. The process of claim 32, wherein said host cell is a coryneform bacterium.

34. The process of claim 32, wherein the host cell further comprises at least one overexpressed gene selected from the group consisting of the lysC gene which codes for a feed bank resistant aspartate kinase, the gap gene which codes for glycerolaldehyde 3-phosphate dehydrogenase, the pgk gene which codes for 3-phosphoglycerate kinase, the pyc gene which codes for pyruvate carboxylase, the tpi gene which codes for triose phosphate isomerase, the metA gene which codes for homoserine O-acetyltransferase, the metB gene which codes for cystathionine gamma-synthase, the aecD gene which codes for cystathionine gamma-lyase, the glyA gene which codes for serine hydroxymethyltransferase, and the metY gene which codes for O-acetylhomoserine-sulfhydrylase.

35. The process of claim 32, wherein the host cell comprises expression of at least one gene whose expression is reduced relative to expression in a wildtype host cell, wherein the at least one gene is selected from the group consisting of the thrB gene which codes for homoserine kinase, the ilvA gene which codes for threonine dehydratase, the thrC gene which codes for threonine synthase, the ddh gene which codes for meso-diaminopimelate D-dehydrogenase, the pck gene which codes for phosphoenol pyruvate carboxykinase, the pgi gene which codes for glucose 6-phosphate isomerase, and the poxB gene which codes for pyruvate oxidase.

36. The process of claim 32, further comprising:
removing an amount of 0 to 100 wt. % of the biomass formed during the culturing from the medium;
concentrating the resulting medium containing the L-methionine; and optionally drying the concentrated medium.

37. A process for producing in L-amino acid which is L-methionine comprising
culturing the host cell of claim 19 in a medium suitable for producing L-methionine; and
collecting the L-methionine produced, wherein the isolated polynucleotide is overexpressed in said host cell.

38. The process of claim 37, wherein said host cell is a coryneform bacterium.

39. The process of claim 37, wherein the host cell further comprises at least one overexpressed gene selected from the group consisting of the lysC gene which codes for a feed back resistant aspartate kinase, the gap gene which codes for glycerolaldehyde 3-phosphate dehydrogenase, the pgk gene which codes for 3-phosphoglycerate kinase, the pyc gene which codes for pyruvate carboxylase; the tpi gene which codes for triose phosphate isomerase, the metA gene which codes for homoserine O-acetyltransferase, the metB gene which codes for cystathionine gamma-synthase, the aecD gene which codes for cystathionine gamma-lyase, the glyA gene which codes for serine hydroxymethyltransferase, and the metY gene which codes for O-acetylhomoserine-sulfhydrylase.

40. The process of claim 37, wherein the host cell comprises at least one gene whose expression is reduced relative to expression in a wildtype host cell wherein the at least one gene is selected from the group consisting of the thrB gene which codes for homoserine kinase, the ilvA gene which codes for threonine dehydratase, the thrC gene which codes for threonine synthase, the ddh gene which codes for meso-diaminopimelate D-dehydrogenase, the pck gene which codes for phosphoenol pyruvate carboxykinase, the pgi gene which codes for glucose 6-phosphate isomerase, and the poxB gene which codes for pyruvate oxidase.

41. The process of claim 37, further comprising:
removing an amount of 0 to 100 wt. % of the biomass formed during the culturing from the medium;
concentrating the resulting medium containing the L-methionine; and optionally
drying the concentrated medium.

42. *Escherichia coli* strain DSM 14354.

43. A polynucleotide consisting of at least 100 consecutive nucleotides of SEQ ID NO: 1, which acts as a probe or primer.

44. The method of claim 32, wherein said polynucleotide is overexpressed by increasing its copy number in said host cell.

* * * * *

SEQUENCE LISTING

<160> NUMBER OF SEQ ID NOS: 4

<210> SEQ ID NO 1
<211> LENGTH: 4301
<212> TYPE: DNA
<213> ORGANISM: Corynebacterium glutamicum
<220> FEATURE:
<221> NAME/KEY: CDS
<222> LOCATION: (385)..(4047)
<223> OTHER INFORMATION:

<400> SEQUENCE: 1

```
taagggtttt ggaggcattg gccgcgaacc catcgctggt catcccgggt ttgcgcatgc      60
cacgttcgta ttcataacca atcgcgatgc cttgagccca ccagccactg acatcaaagt     120
tgtccacgat gtgctttgcg atgtgggtgt gagtccaaga ggtggctttt acgtcgtcaa     180
gcaattttag ccactcttcc cacggctttc cggtgccgtt gaggatagct tcaggggaca     240
tgcctggtgt tgagccttgc ggagtggagt cagtcatgcg accgagacta gtggcgcttt     300
gcctgtgttg cttaggcggc gttgaaaatg aactacgaat gaaaagttcg ggaattgtct     360
aatccgtact aagctgtcta caca atg tct act tca gtt act tca cca gcc       411
                            Met Ser Thr Ser Val Thr Ser Pro Ala
                              1               5
cac aac aac gca cat tcc tcc gaa ttt ttg gat gcg ttg gca aac cat      459
His Asn Asn Ala His Ser Ser Glu Phe Leu Asp Ala Leu Ala Asn His
 10                  15                  20                  25
gtg ttg atc ggc gac ggc gcc atg ggc acc cag ctc caa ggc ttt gac      507
Val Leu Ile Gly Asp Gly Ala Met Gly Thr Gln Leu Gln Gly Phe Asp
                 30                  35                  40
ctg gac gtg gaa aag gat ttc ctt gat ctg gag ggg tgt aat gag att      555
Leu Asp Val Glu Lys Asp Phe Leu Asp Leu Glu Gly Cys Asn Glu Ile
             45                  50                  55
ctc aac gac acc cgc cct gat gtg ttg agg cag att cac cgc gcc tac      603
Leu Asn Asp Thr Arg Pro Asp Val Leu Arg Gln Ile His Arg Ala Tyr
         60                  65                  70
ttt gag gcg gga gct gac ttg gtt gag acc aat act ttt ggt tgc aac      651
Phe Glu Ala Gly Ala Asp Leu Val Glu Thr Asn Thr Phe Gly Cys Asn
     75                  80                  85
ctg ccg aac ttg gcg gat tat gac atc gct gat cgt tgc cgt gag ctt      699
Leu Pro Asn Leu Ala Asp Tyr Asp Ile Ala Asp Arg Cys Arg Glu Leu
 90                  95                 100                 105
gcc tac aag ggc act gca gtg gct agg gaa gtg gct gat gag atg ggg      747
Ala Tyr Lys Gly Thr Ala Val Ala Arg Glu Val Ala Asp Glu Met Gly
                110                 115                 120
ccg ggc cga aac ggc atg cgg cgt ttc gtg gtt ggt tcc ctg gga cct      795
Pro Gly Arg Asn Gly Met Arg Arg Phe Val Val Gly Ser Leu Gly Pro
            125                 130                 135
gga acg aag ctt cca tcg ctg ggc cat gca ccg tat gca gat ttg cgt      843
Gly Thr Lys Leu Pro Ser Leu Gly His Ala Pro Tyr Ala Asp Leu Arg
        140                 145                 150
ggg cac tac aag gaa gca gcg ctt ggc atc atc gac ggt ggt ggc gat      891
Gly His Tyr Lys Glu Ala Ala Leu Gly Ile Ile Asp Gly Gly Gly Asp
    155                 160                 165
gcc ttt ttg att gag act gct cag gac ttg ctt cag gtc aag gct gcg      939
Ala Phe Leu Ile Glu Thr Ala Gln Asp Leu Leu Gln Val Lys Ala Ala
170                 175                 180                 185
gtt cac ggc gtt caa gat gcc atg gct gaa ctt gat aca ttc ttg ccc      987
Val His Gly Val Gln Asp Ala Met Ala Glu Leu Asp Thr Phe Leu Pro
                190                 195                 200
```

```
att att tgc cac gtc acc gta gag acc acc ggc acc atg ctc atg ggt       1035
Ile Ile Cys His Val Thr Val Glu Thr Thr Gly Thr Met Leu Met Gly
            205                 210                 215 tct gag atc ggt gcc gcg ttg aca gcg ctg cag cca ctg ggt atc gac       1083
Ser Glu Ile Gly Ala Ala Leu Thr Ala Leu Gln Pro Leu Gly Ile Asp
        220                 225                 230 atg att ggt ctg aac tgc gcc acc ggc cca gat gag atg agc gag cac       1131
Met Ile Gly Leu Asn Cys Ala Thr Gly Pro Asp Glu Met Ser Glu His
    235                 240                 245 ctg cgt tac ctg tcc aag cac gcc gat att cct gtc tcg gtg atg cct       1179
Leu Arg Tyr Leu Ser Lys His Ala Asp Ile Pro Val Ser Val Met Pro
250                 255                 260                 265 aac gca ggt ctt cct gtc ctg ggt aaa aac ggt gca gaa tac cca ctt       1227
Asn Ala Gly Leu Pro Val Leu Gly Lys Asn Gly Ala Glu Tyr Pro Leu
                270                 275                 280 gag gct gag gat ttg gcg cag gcg ctg gct gga ttc gtc tcc gaa tat       1275
Glu Ala Glu Asp Leu Ala Gln Ala Leu Ala Gly Phe Val Ser Glu Tyr
            285                 290                 295 ggc ctg tcc atg gtg ggt ggt tgt tgt ggc acc aca cct gag cac atc       1323
Gly Leu Ser Met Val Gly Gly Cys Cys Gly Thr Thr Pro Glu His Ile
        300                 305                 310 cgt gcg gtc cgc gat gcg gtg gtt ggt gtt cca gag cag gaa acc tcc       1371
Arg Ala Val Arg Asp Ala Val Val Gly Val Pro Glu Gln Glu Thr Ser
    315                 320                 325 aca ctg acc aag atc cct gca ggc cct gtt gag cag gcc tcc cgc gag       1419
Thr Leu Thr Lys Ile Pro Ala Gly Pro Val Glu Gln Ala Ser Arg Glu
330                 335                 340                 345 gtg gag aaa gag gac tcc gtc gcg tcg ctg tac acc tcg gtg cca ttg       1467
Val Glu Lys Glu Asp Ser Val Ala Ser Leu Tyr Thr Ser Val Pro Leu
                350                 355                 360 tcc cag gaa acc ggc att tcc atg atc ggt gag cgc acc aac tcc aac       1515
Ser Gln Glu Thr Gly Ile Ser Met Ile Gly Glu Arg Thr Asn Ser Asn
            365                 370                 375 ggt tcc aag gca ttc cgt gag gca atg ctg tct ggc gat tgg gaa aag       1563
Gly Ser Lys Ala Phe Arg Glu Ala Met Leu Ser Gly Asp Trp Glu Lys
        380                 385                 390 tgt gtg gat att gcc aag cag caa acc cgc gat ggt gca cac atg ctg       1611
Cys Val Asp Ile Ala Lys Gln Gln Thr Arg Asp Gly Ala His Met Leu
    395                 400                 405 gat ctt tgt gtg gat tac gtg gga cga gac ggc acc gcc gat atg gcg       1659
Asp Leu Cys Val Asp Tyr Val Gly Arg Asp Gly Thr Ala Asp Met Ala
410                 415                 420                 425 acc ttg gca gca ctt ctt gct acc agc tcc act ttg cca atc atg att       1707
Thr Leu Ala Ala Leu Leu Ala Thr Ser Ser Thr Leu Pro Ile Met Ile
                430                 435                 440 gac tcc acc gag cca gag gtt att cgc aca ggc ctt gag cac ttg ggt       1755
Asp Ser Thr Glu Pro Glu Val Ile Arg Thr Gly Leu Glu His Leu Gly
            445                 450                 455 gga cga agc atc gtt aac tcc gtc aac ttt gaa gac ggc gat ggc cct       1803
Gly Arg Ser Ile Val Asn Ser Val Asn Phe Glu Asp Gly Asp Gly Pro
        460                 465                 470 gag tcc cgc tac cag cgc atc atg aaa ctg gta aag cag cac ggt gcg       1851
Glu Ser Arg Tyr Gln Arg Ile Met Lys Leu Val Lys Gln His Gly Ala
    475                 480                 485 gcc gtg gtt gcg ctg acc att gat gag gaa ggc cag gca cgt acc gct       1899
Ala Val Val Ala Leu Thr Ile Asp Glu Glu Gly Gln Ala Arg Thr Ala
490                 495                 500                 505 gag cac aag gtg cgc att gct aaa cga ctg att gac gat atc acc ggc       1947
Glu His Lys Val Arg Ile Ala Lys Arg Leu Ile Asp Asp Ile Thr Gly
                510                 515                 520
```

```
                                                        -continued agc tac ggc ctg gat atc aaa gac atc gtt gtg gac tgc ctg acc ttc    1995
Ser Tyr Gly Leu Asp Ile Lys Asp Ile Val Val Asp Cys Leu Thr Phe
        525                 530                 535 ccg atc tct act ggc cag gaa gaa acc agg cga gat ggc att gaa acc    2043
Pro Ile Ser Thr Gly Gln Glu Glu Thr Arg Arg Asp Gly Ile Glu Thr
540                 545                 550 atc gaa gcc atc cgc gag ctg aag aag ctc tac cca gaa atc cac acc    2091
Ile Glu Ala Ile Arg Glu Leu Lys Lys Leu Tyr Pro Glu Ile His Thr
        555                 560                 565 acc ctg ggt ctg tcc aat att tcc ttc ggc ctg aac cct gct gca cgc    2139
Thr Leu Gly Leu Ser Asn Ile Ser Phe Gly Leu Asn Pro Ala Ala Arg
570                 575                 580                 585 cag gtt ctt aac tct gtg ttc ctc aat gag tgc att gag gct ggt ctg    2187
Gln Val Leu Asn Ser Val Phe Leu Asn Glu Cys Ile Glu Ala Gly Leu
                590                 595                 600 gac tct gcg att gcg cac agc tcc aag att ttg ccg atg aac cgc att    2235
Asp Ser Ala Ile Ala His Ser Ser Lys Ile Leu Pro Met Asn Arg Ile
            605                 610                 615 gat gat cgc cag cgc gaa gtg gcg ttg gat atg gtc tat gat cgc cgc    2283
Asp Asp Arg Gln Arg Glu Val Ala Leu Asp Met Val Tyr Asp Arg Arg
                620                 625                 630 acc gag gat tac gat ccg ctg cag gaa ttc atg cag ctg ttt gag ggc    2331
Thr Glu Asp Tyr Asp Pro Leu Gln Glu Phe Met Gln Leu Phe Glu Gly
635                 640                 645 gtt tct gct gcc gat gcc aag gat gct cgc gct gaa cag ctg gcc gct    2379
Val Ser Ala Ala Asp Ala Lys Asp Ala Arg Ala Glu Gln Leu Ala Ala
650                 655                 660                 665 atg cct ttg ttt gag cgt ttg gca cag cgc atc atc gac ggc gat aag    2427
Met Pro Leu Phe Glu Arg Leu Ala Gln Arg Ile Ile Asp Gly Asp Lys
                670                 675                 680 aat ggc ctt gag gat gat ctg gaa gca ggc atg aag gag aag tct cct    2475
Asn Gly Leu Glu Asp Asp Leu Glu Ala Gly Met Lys Glu Lys Ser Pro
            685                 690                 695 att gcg atc atc aac gag gac ctt ctc aac ggc atg aag acc gtg ggt    2523
Ile Ala Ile Ile Asn Glu Asp Leu Leu Asn Gly Met Lys Thr Val Gly
        700                 705                 710 gag ctg ttt ggt tcc gga cag atg cag ctg cca ttc gtg ctg caa tcg    2571
Glu Leu Phe Gly Ser Gly Gln Met Gln Leu Pro Phe Val Leu Gln Ser
715                 720                 725 gca gaa acc atg aaa act gcg gtg gcc tat ttg gaa ccg ttc atg gaa    2619
Ala Glu Thr Met Lys Thr Ala Val Ala Tyr Leu Glu Pro Phe Met Glu
730                 735                 740                 745 gag gaa gca gaa gct acc gga tct gcg cag gca gag ggc aag ggc aaa    2667
Glu Glu Ala Glu Ala Thr Gly Ser Ala Gln Ala Glu Gly Lys Gly Lys
                750                 755                 760 atc gtc gtg gcc acc gtc aag ggt gac gtg cac gat atc ggc aag aac    2715
Ile Val Val Ala Thr Val Lys Gly Asp Val His Asp Ile Gly Lys Asn
            765                 770                 775 ttg gtg gac atc att ttg tcc aac aac ggt tac gac gtg gtg aac ttg    2763
Leu Val Asp Ile Ile Leu Ser Asn Asn Gly Tyr Asp Val Val Asn Leu
        780                 785                 790 ggc atc aag cag cca ctg tcc gcc atg ttg gaa gca gcg gaa gaa cac    2811
Gly Ile Lys Gln Pro Leu Ser Ala Met Leu Glu Ala Ala Glu Glu His
795                 800                 805 aaa gca gac gtc atc ggc atg tcg gga ctt ctt gtg aag tcc acc gtg    2859
Lys Ala Asp Val Ile Gly Met Ser Gly Leu Leu Val Lys Ser Thr Val
810                 815                 820                 825 gtg atg aag gaa aac ctt gag gag atg aac aac gcc ggc gca tcc aat    2907
Val Met Lys Glu Asn Leu Glu Glu Met Asn Asn Ala Gly Ala Ser Asn
```

-continued

| | | | |
|---|---|---|---|
| | 830 | 835 | 840 |
| tac cca gtc att ttg ggt ggc gct gcg ctg acg cgt acc tac gtg gaa<br>Tyr Pro Val Ile Leu Gly Gly Ala Ala Leu Thr Arg Thr Tyr Val Glu<br>               845                    850                    855 | | | 2955 |
| aac gat ctc aac gag gtg tac acc ggt gag gtg tac tac gcc cgt gat<br>Asn Asp Leu Asn Glu Val Tyr Thr Gly Glu Val Tyr Tyr Ala Arg Asp<br>        860                    865                    870 | | | 3003 |
| gct ttc gag ggc ctg cgc ctg atg gat gag gtg atg gca gaa aag cgt<br>Ala Phe Glu Gly Leu Arg Leu Met Asp Glu Val Met Ala Glu Lys Arg<br>     875                    880                    885 | | | 3051 |
| ggt gaa gga ctt gat ccc aac tca cca gaa gct att gag cag gcg aag<br>Gly Glu Gly Leu Asp Pro Asn Ser Pro Glu Ala Ile Glu Gln Ala Lys<br>890                    895                    900                    905 | | | 3099 |
| aag aag gcg gaa cgt aag gct cgt aat gag cgt tcc cgc aag att gcc<br>Lys Lys Ala Glu Arg Lys Ala Arg Asn Glu Arg Ser Arg Lys Ile Ala<br>                910                    915                    920 | | | 3147 |
| gcg gag cgt aaa gct aat gcg gct ccc gtg att gtt ccg gag cgt tct<br>Ala Glu Arg Lys Ala Asn Ala Ala Pro Val Ile Val Pro Glu Arg Ser<br>     925                    930                    935 | | | 3195 |
| gat gtc tcc acc gat act cca acc gcg gca cca ccg ttc tgg gga acc<br>Asp Val Ser Thr Asp Thr Pro Thr Ala Ala Pro Pro Phe Trp Gly Thr<br>        940                    945                    950 | | | 3243 |
| cgc att gtc aag ggt ctg ccc ttg gcg gag ttc ttg ggc aac ctt gat<br>Arg Ile Val Lys Gly Leu Pro Leu Ala Glu Phe Leu Gly Asn Leu Asp<br>955                    960                    965 | | | 3291 |
| gag cgc gcc ttg ttc atg ggg cag tgg ggt ctg aaa tcc acc cgc ggc<br>Glu Arg Ala Leu Phe Met Gly Gln Trp Gly Leu Lys Ser Thr Arg Gly<br>970                    975                    980                    985 | | | 3339 |
| aac gag ggt cca agc tat gag gat ttg gtg gaa act gaa ggc cga cca<br>Asn Glu Gly Pro Ser Tyr Glu Asp Leu Val Glu Thr Glu Gly Arg Pro<br>                990                    995                  1000 | | | 3387 |
| cgc ctg cgc tac tgg ctg gat cgc ctg aag tct gag ggc att ttg<br>Arg Leu Arg Tyr Trp Leu Asp Arg Leu Lys Ser Glu Gly Ile Leu<br>                   1005                  1010                  1015 | | | 3432 |
| gac cac gtg gcc ttg gtg tat ggc tac ttc cca gcg gtc gcg gaa<br>Asp His Val Ala Leu Val Tyr Gly Tyr Phe Pro Ala Val Ala Glu<br>                 1020                  1025                  1030 | | | 3477 |
| ggc gat gac gtg gtg atc ttg gaa tcc ccg gat cca cac gca gcc<br>Gly Asp Asp Val Val Ile Leu Glu Ser Pro Asp Pro His Ala Ala<br>                 1035                  1040                  1045 | | | 3522 |
| gaa cgc atg cgc ttt agc ttc cca cgc cag cag cgc ggc agg ttc<br>Glu Arg Met Arg Phe Ser Phe Pro Arg Gln Gln Arg Gly Arg Phe<br>                 1050                  1055                  1060 | | | 3567 |
| ttg tgc atc gcg gat ttc att cgc cca cgc gag caa gct gtc aag<br>Leu Cys Ile Ala Asp Phe Ile Arg Pro Arg Glu Gln Ala Val Lys<br>                 1065                  1070                  1075 | | | 3612 |
| gac ggc caa gtg gac gtc atg cca ttc cag ctg gtc acc atg ggt<br>Asp Gly Gln Val Asp Val Met Pro Phe Gln Leu Val Thr Met Gly<br>                 1080                  1085                  1090 | | | 3657 |
| aat cct att gct gat ttc gcc aac gag ttg ttc gca gcc aat gaa<br>Asn Pro Ile Ala Asp Phe Ala Asn Glu Leu Phe Ala Ala Asn Glu<br>                 1095                  1100                  1105 | | | 3702 |
| tac cgc gag tac ttg gaa gtt cac ggc atc ggc gtg cag ctc acc<br>Tyr Arg Glu Tyr Leu Glu Val His Gly Ile Gly Val Gln Leu Thr<br>                 1110                  1115                  1120 | | | 3747 |
| gaa gca ttg gcc gag tac tgg cac tcc cga gtg cgc agc gaa ctc<br>Glu Ala Leu Ala Glu Tyr Trp His Ser Arg Val Arg Ser Glu Leu<br>                 1125                  1130                  1135 | | | 3792 |
| aag ctg aac gac ggt gga tct gtc gct gat ttt gat cca gaa gac | | | 3837 |

-continued

```
Lys Leu Asn Asp Gly Gly Ser Val Ala Asp Phe Asp Pro Glu Asp
            1140                1145                1150 aag acc aag ttc ttc gac ctg gat tac cgc ggc gcc cgc ttc tcc       3882
Lys Thr Lys Phe Phe Asp Leu Asp Tyr Arg Gly Ala Arg Phe Ser
            1155                1160                1165 ttt ggt tac ggt tct tgc cct gat ctg gaa gac cgc gca aag ctg       3927
Phe Gly Tyr Gly Ser Cys Pro Asp Leu Glu Asp Arg Ala Lys Leu
            1170                1175                1180 gtg gaa ttg ctc gag cca ggc cgt atc ggc gtg gag ttg tcc gag       3972
Val Glu Leu Leu Glu Pro Gly Arg Ile Gly Val Glu Leu Ser Glu
            1185                1190                1195 gaa ctc cag ctg cac cca gag cag tcc aca gac gcg ttt gtg ctc       4017
Glu Leu Gln Leu His Pro Glu Gln Ser Thr Asp Ala Phe Val Leu
            1200                1205                1210 tac cac cca gag gca aag tac ttt aac gtc taacaccttt gagagggaaa     4067
Tyr His Pro Glu Ala Lys Tyr Phe Asn Val
            1215                1220 actttcccgc acattgcaga tcgtgccact ttaactaagg ttgacggcat gattaaggcg  4127
attttctggg acatggacgg cacgatggtg gactctgagc cacagtgggg cattgctacc  4187
tacgagctca gcgaagccat gggccgccgc ctcaccccgg agctccggga actcaccgtc  4247
ggctcgagcc tgccgcgcac catgcgctta tgcgcagagc acgcaggcat taca        4301

<210> SEQ ID NO 2
<211> LENGTH: 1221
<212> TYPE: PRT
<213> ORGANISM: Corynebacterium glutamicum

<400> SEQUENCE: 2

Met Ser Thr Ser Val Thr Ser Pro Ala His Asn Asn Ala His Ser Ser
1               5                   10                  15

Glu Phe Leu Asp Ala Leu Ala Asn His Val Leu Ile Gly Asp Gly Ala
            20                  25                  30

Met Gly Thr Gln Leu Gln Gly Phe Asp Leu Asp Val Glu Lys Asp Phe
        35                  40                  45

Leu Asp Leu Glu Gly Cys Asn Glu Ile Leu Asn Asp Thr Arg Pro Asp
    50                  55                  60

Val Leu Arg Gln Ile His Arg Ala Tyr Phe Glu Ala Gly Ala Asp Leu
65                  70                  75                  80

Val Glu Thr Asn Thr Phe Gly Cys Asn Leu Pro Asn Leu Ala Asp Tyr
                85                  90                  95

Asp Ile Ala Asp Arg Cys Arg Glu Leu Ala Tyr Lys Gly Thr Ala Val
            100                 105                 110

Ala Arg Glu Val Ala Asp Glu Met Gly Pro Gly Arg Asn Gly Met Arg
        115                 120                 125

Arg Phe Val Val Gly Ser Leu Gly Pro Gly Thr Lys Leu Pro Ser Leu
    130                 135                 140

Gly His Ala Pro Tyr Ala Asp Leu Arg Gly His Tyr Lys Glu Ala Ala
145                 150                 155                 160

Leu Gly Ile Ile Asp Gly Gly Asp Ala Phe Leu Ile Glu Thr Ala
                165                 170                 175

Gln Asp Leu Leu Gln Val Lys Ala Ala Val His Gly Val Gln Asp Ala
            180                 185                 190

Met Ala Glu Leu Asp Thr Phe Leu Pro Ile Ile Cys His Val Thr Val
        195                 200                 205

Glu Thr Thr Gly Thr Met Leu Met Gly Ser Glu Ile Gly Ala Ala Leu
```

```
            210                 215                 220
Thr Ala Leu Gln Pro Leu Gly Ile Asp Met Ile Gly Leu Asn Cys Ala
225                 230                 235                 240

Thr Gly Pro Asp Glu Met Ser Glu His Leu Arg Tyr Leu Ser Lys His
                245                 250                 255

Ala Asp Ile Pro Val Ser Val Met Pro Asn Ala Gly Leu Pro Val Leu
                260                 265                 270

Gly Lys Asn Gly Ala Glu Tyr Pro Leu Glu Ala Glu Asp Leu Ala Gln
                275                 280                 285

Ala Leu Ala Gly Phe Val Ser Glu Tyr Gly Leu Ser Met Val Gly Gly
290                 295                 300

Cys Cys Gly Thr Thr Pro Glu His Ile Arg Ala Val Arg Asp Ala Val
305                 310                 315                 320

Val Gly Val Pro Glu Gln Glu Thr Ser Thr Leu Thr Lys Ile Pro Ala
                325                 330                 335

Gly Pro Val Glu Gln Ala Ser Arg Glu Val Glu Lys Glu Asp Ser Val
                340                 345                 350

Ala Ser Leu Tyr Thr Ser Val Pro Leu Ser Gln Glu Thr Gly Ile Ser
                355                 360                 365

Met Ile Gly Glu Arg Thr Asn Ser Asn Gly Ser Lys Ala Phe Arg Glu
370                 375                 380

Ala Met Leu Ser Gly Asp Trp Glu Lys Cys Val Asp Ile Ala Lys Gln
385                 390                 395                 400

Gln Thr Arg Asp Gly Ala His Met Leu Asp Leu Cys Val Asp Tyr Val
                405                 410                 415

Gly Arg Asp Gly Thr Ala Asp Met Ala Thr Leu Ala Ala Leu Leu Ala
                420                 425                 430

Thr Ser Ser Thr Leu Pro Ile Met Ile Asp Ser Thr Glu Pro Glu Val
                435                 440                 445

Ile Arg Thr Gly Leu Glu His Leu Gly Gly Arg Ser Ile Val Asn Ser
                450                 455                 460

Val Asn Phe Glu Asp Gly Asp Gly Pro Glu Ser Arg Tyr Gln Arg Ile
465                 470                 475                 480

Met Lys Leu Val Lys Gln His Gly Ala Ala Val Val Ala Leu Thr Ile
                485                 490                 495

Asp Glu Glu Gly Gln Ala Arg Thr Ala Glu His Lys Val Arg Ile Ala
                500                 505                 510

Lys Arg Leu Ile Asp Asp Ile Thr Gly Ser Tyr Gly Leu Asp Ile Lys
                515                 520                 525

Asp Ile Val Val Asp Cys Leu Thr Phe Pro Ile Ser Thr Gly Gln Glu
                530                 535                 540

Glu Thr Arg Arg Asp Gly Ile Glu Thr Ile Glu Ala Ile Arg Glu Leu
545                 550                 555                 560

Lys Lys Leu Tyr Pro Glu Ile His Thr Thr Leu Gly Leu Ser Asn Ile
                565                 570                 575

Ser Phe Gly Leu Asn Pro Ala Ala Arg Gln Val Leu Asn Ser Val Phe
                580                 585                 590

Leu Asn Glu Cys Ile Glu Ala Gly Leu Asp Ser Ala Ile Ala His Ser
                595                 600                 605

Ser Lys Ile Leu Pro Met Asn Arg Ile Asp Asp Arg Gln Arg Glu Val
                610                 615                 620

Ala Leu Asp Met Val Tyr Asp Arg Arg Thr Glu Asp Tyr Asp Pro Leu
625                 630                 635                 640
```

-continued

```
Gln Glu Phe Met Gln Leu Phe Glu Gly Val Ser Ala Ala Asp Ala Lys
                645                 650                 655

Asp Ala Arg Ala Glu Gln Leu Ala Ala Met Pro Leu Phe Glu Arg Leu
            660                 665                 670

Ala Gln Arg Ile Ile Asp Gly Asp Lys Asn Gly Leu Glu Asp Asp Leu
        675                 680                 685

Glu Ala Gly Met Lys Glu Lys Ser Pro Ile Ala Ile Asn Glu Asp
    690                 695                 700

Leu Leu Asn Gly Met Lys Thr Val Gly Glu Leu Phe Gly Ser Gly Gln
705                 710                 715                 720

Met Gln Leu Pro Phe Val Leu Gln Ser Ala Glu Thr Met Lys Thr Ala
                725                 730                 735

Val Ala Tyr Leu Glu Pro Phe Met Glu Glu Ala Glu Ala Thr Gly
            740                 745                 750

Ser Ala Gln Ala Glu Gly Lys Gly Lys Ile Val Ala Thr Val Lys
        755                 760                 765

Gly Asp Val His Asp Ile Gly Lys Asn Leu Val Asp Ile Ile Leu Ser
    770                 775                 780

Asn Asn Gly Tyr Asp Val Val Asn Leu Gly Ile Lys Gln Pro Leu Ser
785                 790                 795                 800

Ala Met Leu Glu Ala Ala Glu His Lys Ala Asp Val Ile Gly Met
                805                 810                 815

Ser Gly Leu Leu Val Lys Ser Thr Val Val Met Lys Glu Asn Leu Glu
            820                 825                 830

Glu Met Asn Asn Ala Gly Ala Ser Asn Tyr Pro Val Ile Leu Gly Gly
        835                 840                 845

Ala Ala Leu Thr Arg Thr Tyr Val Glu Asn Asp Leu Asn Glu Val Tyr
    850                 855                 860

Thr Gly Glu Val Tyr Tyr Ala Arg Asp Ala Phe Glu Gly Leu Arg Leu
865                 870                 875                 880

Met Asp Glu Val Met Ala Glu Lys Arg Gly Glu Gly Leu Asp Pro Asn
                885                 890                 895

Ser Pro Glu Ala Ile Glu Gln Ala Lys Lys Ala Glu Arg Lys Ala
            900                 905                 910

Arg Asn Glu Arg Ser Arg Lys Ile Ala Ala Glu Arg Lys Ala Asn Ala
        915                 920                 925

Ala Pro Val Ile Val Pro Glu Arg Ser Asp Val Ser Thr Asp Thr Pro
    930                 935                 940

Thr Ala Ala Pro Pro Phe Trp Gly Thr Arg Ile Val Lys Gly Leu Pro
945                 950                 955                 960

Leu Ala Glu Phe Leu Gly Asn Leu Asp Glu Arg Ala Leu Phe Met Gly
                965                 970                 975

Gln Trp Gly Leu Lys Ser Thr Arg Gly Asn Glu Gly Pro Ser Tyr Glu
            980                 985                 990

Asp Leu Val Glu Thr Glu Gly Arg Pro Arg Leu Arg Tyr Trp Leu Asp
        995                 1000                1005

Arg Leu Lys Ser Glu Gly Ile Leu Asp His Val Ala Leu Val Tyr
    1010                1015                1020

Gly Tyr Phe Pro Ala Val Ala Glu Gly Asp Asp Val Val Ile Leu
    1025                1030                1035

Glu Ser Pro Asp Pro His Ala Ala Glu Arg Met Arg Phe Ser Phe
    1040                1045                1050
```

-continued

```
Pro Arg Gln Gln Arg Gly Arg Phe Leu Cys Ile Ala Asp Phe Ile
    1055                1060                1065

Arg Pro Arg Glu Gln Ala Val Lys Asp Gly Gln Val Asp Val Met
    1070                1075                1080

Pro Phe Gln Leu Val Thr Met Gly Asn Pro Ile Ala Asp Phe Ala
    1085                1090                1095

Asn Glu Leu Phe Ala Ala Asn Glu Tyr Arg Glu Tyr Leu Glu Val
    1100                1105                1110

His Gly Ile Gly Val Gln Leu Thr Glu Ala Leu Ala Glu Tyr Trp
    1115                1120                1125

His Ser Arg Val Arg Ser Glu Leu Lys Leu Asn Asp Gly Gly Ser
    1130                1135                1140

Val Ala Asp Phe Asp Pro Glu Asp Lys Thr Lys Phe Phe Asp Leu
    1145                1150                1155

Asp Tyr Arg Gly Ala Arg Phe Ser Phe Gly Tyr Gly Ser Cys Pro
    1160                1165                1170

Asp Leu Glu Asp Arg Ala Lys Leu Val Glu Leu Leu Glu Pro Gly
    1175                1180                1185

Arg Ile Gly Val Glu Leu Ser Glu Glu Leu Gln Leu His Pro Glu
    1190                1195                1200

Gln Ser Thr Asp Ala Phe Val Leu Tyr His Pro Glu Ala Lys Tyr
    1205                1210                1215

Phe Asn Val
    1220

<210> SEQ ID NO 3
<211> LENGTH: 52
<212> TYPE: DNA
<213> ORGANISM: Artificial sequence
<220> FEATURE:
<223> OTHER INFORMATION: Synthetic DNA

<400> SEQUENCE: 3
gatctaagat ctaaaggagg acaaccatgt ctacttcagt tacttcacca gc          52

<210> SEQ ID NO 4
<211> LENGTH: 32
<212> TYPE: DNA
<213> ORGANISM: Artificial sequence
<220> FEATURE:
<223> OTHER INFORMATION: Synthetic DNA

<400> SEQUENCE: 4
gatctagtcg acccctctca aaggtgttag ac                                32
```